(12) United States Patent
Shalyt

(10) Patent No.: US 10,590,560 B1
(45) Date of Patent: Mar. 17, 2020

(54) CONTROL OF ADDITIVE TURNOVER IN AN ELECTRODEPOSITION SOLUTION

(71) Applicant: ECI Technology, Inc., Totowa, NJ (US)

(72) Inventor: Eugene Shalyt, Washington Township, NJ (US)

(73) Assignee: ECI Technology, Inc., Totowa, NJ (US)

( * ) Notice: Subject to any disclaimer, the term of this patent is extended or adjusted under 35 U.S.C. 154(b) by 23 days.

(21) Appl. No.: 16/109,388

(22) Filed: Aug. 22, 2018

(51) Int. Cl.
  *C25D 21/12* (2006.01)
  *C25D 3/38* (2006.01)
  *G01N 21/66* (2006.01)

(52) U.S. Cl.
  CPC ............... *C25D 21/12* (2013.01); *C25D 3/38* (2013.01); *G01N 21/66* (2013.01)

(58) Field of Classification Search
  CPC ................................ C25D 21/12; C25D 3/38
  See application file for complete search history.

(56) References Cited

U.S. PATENT DOCUMENTS

| | | |
|---|---|---|
| 4,058,437 A | 11/1977 | Young |
| 4,628,726 A | 12/1986 | Heikkila et al. |
| 5,223,118 A | 6/1993 | Sonnenberg et al. |
| 5,352,350 A | 10/1994 | Andricacos et al. |
| 6,365,033 B1 | 4/2002 | Graham et al. |
| 6,458,262 B1 | 10/2002 | Reid |
| 6,645,364 B2 | 11/2003 | Calvert et al. |
| 6,808,611 B2 | 10/2004 | Sun et al. |
| 7,270,733 B2 | 9/2007 | Wikiel et al. |
| 7,291,253 B2 | 11/2007 | Pavlov et al. |
| 7,531,134 B1 | 5/2009 | Anderson et al. |
| 8,372,258 B2 | 2/2013 | Willey et al. |
| 8,808,521 B2 | 8/2014 | Zhou |
| 9,045,841 B1 | 6/2015 | Buckalew et al. |

(Continued)

FOREIGN PATENT DOCUMENTS

| | | |
|---|---|---|
| EP | 2 937 686 B1 | 3/2017 |
| KR | 101210347 B1 | 1/2013 |
| WO | WO 03/008919 A1 | 1/2003 |

OTHER PUBLICATIONS

Hung et al., "Investigation of Bis-(3-sodiumsulfopropyl disulfide) (SPS) Decomposition in a Copper Electroplating Bath Using Mass Spectroscopy," J. Electrochem. Soc. 155(5):H329-H333, Abstract only (2008).

(Continued)

*Primary Examiner* — Brian W Cohen
*Assistant Examiner* — Ho-Sung Chung
(74) *Attorney, Agent, or Firm* — Baker Botts, L.L.P.

(57) ABSTRACT

Methods for measuring additive turnover in a solution, such as an electrodeposition solution, are provided. Methods for measuring an age or lifetime of a solution, such as an electrodeposition solution, are also provided. Methods can include providing a solution containing an organic additive and a plurality of breakdown products of the organic additive, in which the plurality of breakdown products include at least one active component and at least one inactive component and measuring the concentration of the at least one inactive component in the solution. Methods can further include determining additive turnover of the solution based on the concentration of the at least one inactive component in the solution.

11 Claims, 4 Drawing Sheets

(56) References Cited

U.S. PATENT DOCUMENTS

| | | |
|---|---|---|
| 9,099,582 B2 | 8/2015 | Sun et al. |
| 9,982,357 B2 | 5/2018 | Mayer et al. |
| 2004/0108213 A1 | 6/2004 | Talasek et al. |
| 2006/0166370 A1 | 7/2006 | Bailey et al. |
| 2007/0261963 A1 | 11/2007 | Han et al. |
| 2012/0174827 A1* | 7/2012 | Sekiguchi ................ C01G 3/00 106/480 |
| 2016/0362793 A1 | 12/2016 | Izumi et al. |
| 2018/0016699 A1 | 1/2018 | Arvin et al. |

OTHER PUBLICATIONS

Palmans et al., "Ion-pair chromatography of bis (sodium-sulfopropyl) disulfide brightener in acidic copper plating baths," J Chromatogr A. 1085(1):147-154, Abstract only (2005).

Vereecken et al., "The Chemistry of Additives in Damascene Copper Plating," IBM J. Res. & Dev., 49(1):3-18 (2005).

Volov, "Copper and Copper Alloys: Studies of Additives," Columbia University Academic Commons, 2013 (163 pages).

Zhang et al., "Analysis of electroplating baths by capillary electrophoresis with high voltage contactless conductivity detection," Measurement Science and Technology 17(12): Abstract (2006).

* cited by examiner

CONTROL OF ADDITIVE TURNOVER IN AN ELECTRODEPOSITION SOLUTION

FIELD

The present disclosure relates to methods for control of additive turnover in a solution and to methods for determining a lifetime or an age of a solution, such as an electrodeposition solution.

BACKGROUND

Electrodeposition processes are used in several industries including metal finishing, semiconductor, printed circuit board, and solar industries in order to deposit metal or produce products with desired properties. Electrolytes used for metal deposition processes usually include metal salt (in an amount approx. greater than 1 g/L), a conductive component (e.g., salts, acids, bases, or combinations thereof), pH adjustors and/or buffering agents, and chelating agents. Additionally, electrolytes can include micro-quantities (i.e., less than 1 g/L) of surface active organic additives. The surface organic additives can, for example, modify grain structure, modify grain mechanical properties, provide uniformity of deposits, and provide additional targeted characteristics. In particular, the semiconductor industry has utilized electrodeposited copper as universal interconnect materials for deposits of varying scales, for example, ranging from nanometers (nm) to macro-scales (e.g., inches).

Organic additives can be used in electrodeposition solutions. Organic additives can include, for example, accelerators, brighteners, suppressors and levelers. Accelerators promote defect-free deposits that fill deep or irregular features on the surface to be treated. Accelerators can also be referred to as brighteners. Accelerators and brighteners have a relatively high consumption in electrodeposition processes. Accelerators and brighteners are often used in conjunction with other organic additives, including suppressors and levelers. Suppressors and levelers have relatively low consumption in electrodeposition processes. Suppressors can also be referred to as a carrier, wetter, or leveler. Suppressors can include, for example, polyethylene glycol (PEG). Levelers can include, for example, 8-(4-Dimethylaminophenyl) diazenyl-N,N-diethyl-10-phenylphenazin-10-ium-2-amine chloride (Janus Green B).

For example, accelerators and brighteners can include a sodium salt, such as bis-(3-sulfopropyl) disulfide (SPS, $HSO_3-CH_2-CH_2-CH_2-S-S-CH_2-CH_2-CH_2-SO_3$). During the electrodeposition process, SPS is reduced or oxidized to form several breakdown products. One such breakdown product is 3-mercaptopropyl sulfonate (MPS or MPSA, $HSO_3-CH_2-CH_2-CH_2-SH$). For reference, the chemical structures of SPS and MPS are provided in FIG. 1. The breakdown of SPS to MPS generally proceeds according to Formula 1, below:

$$SPS + 2H^+ + 2e^- \leftrightharpoons 2\ MPS \quad \text{(Formula 1)}$$

Additionally, several other reactions can occur in parallel, as SPS and MPS degrade into other breakdown products. Such breakdown products included mono-ox-SPS, di-ox-SPS, mono-ox-MPS, di-ox-MPS, and propane disulfonic acid (PDS) via additional oxidation and reduction reactions or hydrolysis. A schematic of these reactions is provided in FIG. 2. Additional description of reactions involving SPS and its breakdown products is provided in Igor Volov, 2013, Copper and Copper Alloys: Studies of Additives, Columbia University Academic Commons, available at http://hdl.handle.net/10022/AC:P:15408, which is incorporated by reference herein. Additional description on the chemistry of additives is provided in Vereecken, P. M., et al., The Chemistry of Additives in Damascene Copper Plating, IBM J. Res. & Dev., Vol. 49 No. 1, pages 3-18, January 2005, which is incorporated by reference herein.

A metal electrodeposition process can include an electrodeposition solution including a metal salt and one or more organic additives. The metal salt included in the electrodeposition solution can be quantitatively utilized during the deposition process (e.g., Me(solution)→Me deposit)). However, utilization of the one or more organic additives included in the electrodeposition solution can be relatively difficult to quantify. For example, the one or more organic additives can be reduced and/or oxidized, cleaved, polymerized and/or codeposited, or removed by drag-out. Drag-out is provided in electrodeposition processes which include sequential dipping of a part into multiple solutions. In electrodeposition processes, an electrodeposition step can be proceeded and followed by a cleaning and surface preparation step. As the part is lifted from a process container, solution is carried with the part. Thus, for example, a part will provide a portion of preceding additive solution and remove a portion of electrodeposition solution including an organic additive resulting in a "carry-over" process or drag-out.

Strategies for process metrology strategy include, for example, monitoring of organic additives and breakdown products of the organic additives. Therefrom, a replenishment dose for the organic additive can be calculated and a lifetime of the electrodeposition solution can be determined. In some processes, "metal turnover" can be used as an indicator of age for an electrodeposition solution (e.g., a total amount of metal added over a lifetime of the solution/initial amount of metal in the solution). The total amount of metal added can be calculated as a total metal dose. The process can be used for an operating condition in which the process tank is replenished over its lifetime and then drained. In another process, "bleed and feed" can be used in which a portion of the solution is removed and replaced with a fresh solution (e.g., daily or more frequently). An age of an electrodeposition solution used in a "bleed and feed" process may be relative difficult to determine, for example, if the "bleed and feed" process occurs on a continuous basis.

Degradation of an organic additive can be characterized through multiple methods for determining a concentration of specific individual breakdown products of the organic additive. Therefore, there is a need for an assessment of additive turnover in solutions. For example, a process of measuring total organic carbon (TOC) can be used. The method includes measuring total carbon remaining in solution to determine the age of the solution. Thus, the method fails to measure carbon, for example, that is codeposited, oxidized into carbon dioxide ($CO_2$), or removed by drag-out. Further, industries often provide organic acids and metal organic salts as a large component of electrodeposition solutions, e.g., methanesufionic (MSA) $CH_3-SO_3$ (−) as a substitute for sulfate $SO_4$ (2−). TOC processes monitor large levels of MSA and are not able to detect lower level changes of concentrations of accumulated organics (e.g., changes in ppm). Additionally, when an organometallic component is not used in the electrodeposition solution, carbon load can be unevenly distributed, for example, with a suppressor contributing at least 90% of the total carbon. Thus, TOC processes monitor total accumulation of the suppressor, however, are not able to monitor the accumulation of other micro components in the electrodeposition solution. Other methods describe monitoring the concentrations of inorganic counterions of organic additives in solution to determine and monitor the age of the solution (e.g., measuring sulfate concentration in $CuSO_4$ metal salt of an electrodeposition solution).

However, these techniques can be insufficient in determining an age of a solution to effectively control additive turnover as prior methods provide several methods targeting individual breakdown products of organic additives. Thus, there remains a need for methods for more accurate and comprehensive measurement and control of additive turnover in a solution.

SUMMARY

The presently disclosed subject matter provides methods for the control of additive turnover in an electrodeposition solution. For example, the presently disclosed methods can be used to measure a lifetime of an electrodeposition solution. As embodied herein, methods can include measuring and monitoring of at least one inactive component of an organic additive in an electrodeposition solution, e.g., an acid copper electrodeposition solution. The concentration of the at least one inactive component of the organic additive can be measured as the solution ages and additive turnover of the electrodeposition solution can be determined therefrom.

In certain aspects, the presently disclosed methods include measuring additive turnover of a solution. The methods can include providing a solution containing an organic additive and a plurality of breakdown products of the organic additive. The plurality of breakdown products can include at least one inactive component and at least one active component. The concentration of the at least one inactive component can be measured. The additive turnover of the solution can be determined based on the concentration of the inactive component in the solution.

In certain embodiments, the organic additive can include a brightener, an accelerator, a leveler, a suppressor, a grain refiner, a wetter, a carrier, a stress reducer, a hardener, a softener, or a combination thereof.

In certain embodiments, the at least one inactive component can be an ion.

In certain embodiments, the at least one inactive component can include a metal.

In certain embodiments, the at least one inactive component can include sodium. In certain embodiments, the at least one inactive component can include potassium.

In certain embodiments, the solution can be an electrodeposition solution.

In certain embodiments, the solution can be an acid copper electrodeposition solution.

In certain embodiments, the concentration of the at least one inactive component can be measured by atomic absorbance spectroscopy (AAS), microwave plasma (MP), inductively coupled plasma (ICP), ion chromatography (IC), capillary electrophoresis (CE), or ion selective electrode (ISE) potentiometry.

In certain embodiments, the method further includes adjusting a concentration of the organic component in the solution based on the additive turnover of the solution.

In certain embodiments, the method further includes, based on the additive turnover of the solution, removing at least a portion of the solution and replenishing at least a portion of the solution.

In certain embodiments, the method further includes determining an end of life of the solution based on the additive turnover of the solution.

In certain embodiments, the method further includes adjusting the concentration of the organic component in the solution based on the additive turnover of the solution, metal turnover of the solution, and concentration of at least one active component of the breakdown products of the organic additive.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter. Moreover, the principles of the disclosed subject matter can be implemented in various configurations and are not intended to be limited in any way to the specific embodiments presented herein.

DETAILED DESCRIPTION

Figure 1:
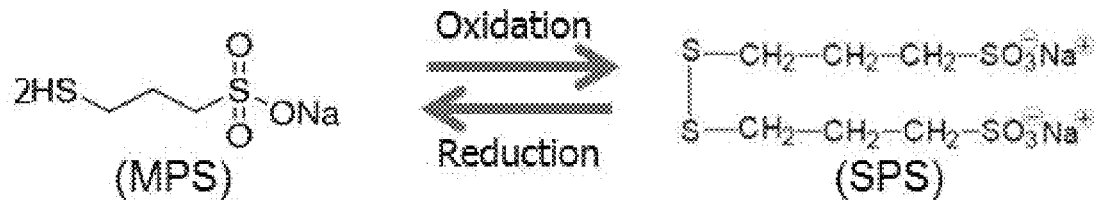
FIG. 1 provides a schematic of the reduction of bis-(3-sulfopropyl) disulfide (SPS) to form the breakdown product 3-mercaptopropyl sulfonate (MPS)
Figure 2:
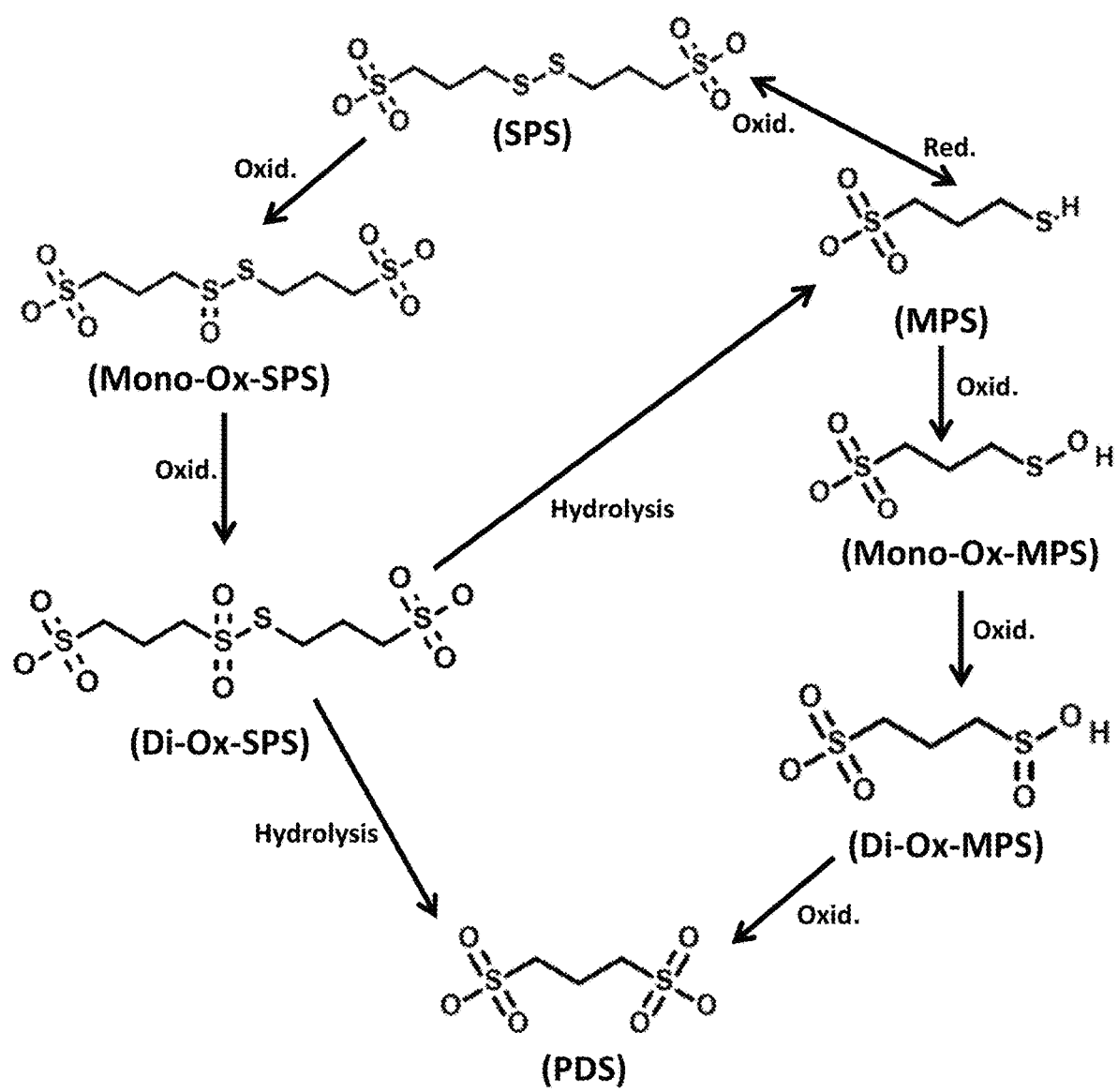
FIG. 2 illustrates further reactions of SPS and MPS to form additional breakdown products.

The present disclosure relates to methods that can be used to measure and monitor additive turnover in a solution. The present disclosure further relates to methods that can be used to determine an age or a lifetime of a solution. For example, the presently disclosure methods can be used for process control during electrodeposition, e.g., during copper electrodeposition. As embodied herein, a concentration of one or more inactive components of an organic additive can be monitored during electrodeposition to optimize the amount of organic additive present in the electrodeposition solution during processing. The electrodeposition solution can be an acid copper electrolyte.

As embodied herein, methods can include providing a solution containing an organic additive and a plurality of breakdown products of the organic additive. The plurality of breakdown products can include at least one inactive component and at least one active component. Methods can further include measuring the concentration of the at least one inactive component. Methods can further include determining a lifetime of the solution based on the concentration of the at least one inactive component in the solution. The presently disclosed methods can determine the total concentration of the at least one inactive component of the organic additive. For example, in solutions where the organic additive is a sodium salt, e.g., bis(sodiumsulfopropyl)disulfide, an organic component of the molecule is consumed by the process whereas the sodium portion of the molecule remains and accumulates in the solution. Thus, the presently disclosed methods can measure and monitor the concentration of the sodium portion of the molecule and approximate the lifetime of the solution and monitor organic additive turnover therefrom. Furthermore, end of life decisions and bleed and feed ratios of the solution can be determined from the approximated lifetime of the solution.

As described above, there is a need in the industry for improved methods of determining additive turnover in a solution, particularly for measuring one or more inactive components of breakdown products of an organic additive included in an electrodeposition solution.

In certain embodiments, the solution is an electrodeposition solution. For example, the solution can be an acid copper acid copper electrodeposition solution. The solution can include one or more organic additives.

The organic additives can include an accelerator, a leveler, a suppressor, a grain refiner, a wetter, a carrier, a stress reducer, a hardener, a softener, or combinations thereof.

When in solution and used in an electrodeposition process, an active component (e.g., an organic portion) of the molecule can be consumed while an inactive component of the molecule can remain and accumulate in the solution. In certain embodiments, the solution is an electrodeposition solution including copper (Cu), silver (Ag), palladium (Pd), gold (Au), cobalt (Co), nickel (Ni), tin (Sn), indium (In) or alloys thereof. Electrolytes can be acidic, alkaline or neutral with or without chelating agents. In monitoring a concentration of the inactive portion of the organic additive, additive turnover, a lifetime of the solution, and adjustments to bleed and feed ratios can be determined. For example, the concentration of the inactive portion of the organic additive can be measured in fresh solution, aged (mid-life) solution, and aged (end-of-life) solution. To calculate additive turnover in the solution, the measured concentration of the inactive portion in the aged (e.g., mid-life or end-of-life) solution can be divided by the measured concentration of the inactive portion in the fresh solution. For example, in an acid copper electrodeposition solution, the concentration of sodium can be monitored as the solution ages and an additive turnover calculated from these measurements as provided above. Additionally, an age or a lifetime of the solution can be determined from the methods provided herein. For example, the methods of the present disclosure can be used to indicate bath ageing. Bath age can be used to determine, for example, if a particular solution is a fresh, mid-aged, or end-of-life solution.

The inactive component of the organic additive can be monitored and measured, for example, by atomic absorbance spectroscopy (AAS), microwave plasma (MP), inductively coupled plasma (ICP), ion chromatography (IC), capillary electrophoresis (CE), ion selective electrode (ISE) potentiometry among other methods.

The presently disclosed subject matter will be better understood by reference to the following Examples. The following examples are merely illustrative of the presently disclosed subject matter and should not be considered as limiting the scope of the subject matter in any way.

EXAMPLES

The following examples are merely illustrative of the presently disclosed subject matter and they should not be considered as limiting the scope of the subject matter in any way.

Example 1: Determination of Additive Turnover in Acid Copper Electrodeposition Solutions (Solution A)

In this Example, the additive turnover of an acid copper electrodeposition solution (Solution A) was measured in accordance with the presently disclosed methods.

Figure 3:
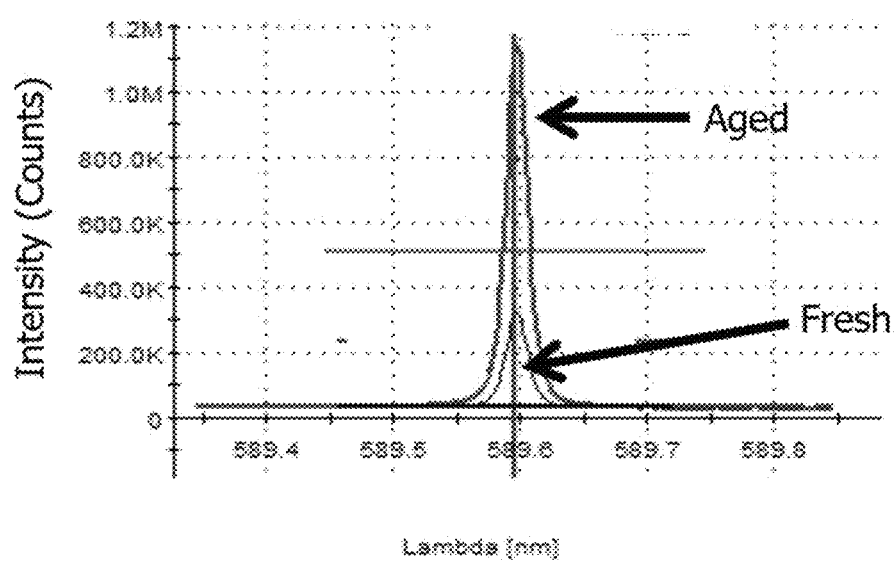
FIG. 3 provides the results of ICP-OES spectrometry measurements for sodium concentration in a fresh and aged (end-of-life) acid copper electrodeposition solution (Solution A) of Example 1.

An acid copper electrodeposition solution (Solution A) used for advanced wafer level packaging was tested. Solution A was a solution for manufacturing of a Cu pillar in a memory device. Sodium concentrations of Solution A were analyzed using a Spectro Blue ICP-OES spectrometer (manufactured by Spectro Analytics®). The sodium peak for Solution A was 589.59 nm, which was used for further analysis. The concentration of sodium was measured in both fresh Solution A and aged (end-of-life) Solution A. Fresh Solution A contained 0.76 mg/L of sodium. Aged (end-of-life) Solution A contained 83 mg/L of sodium. The test results are summarized in FIG. 3. Additive turnover was calculated as follows:

Fresh Solution A sodium concentration: 0.76 mg/L
Aged (end-of-life) Solution A sodium concentration: 83 mg/L
Additive Turnover (end-of-life) Solution A: 83/0.76=109

Example 2: Determination of Additive Turnover in Acid Copper Electrodeposition Solutions (Solution B)

In this Example, the additive turnover of an acid copper electrodeposition solution was measured in accordance with the presently disclosed methods.

Figure 4:
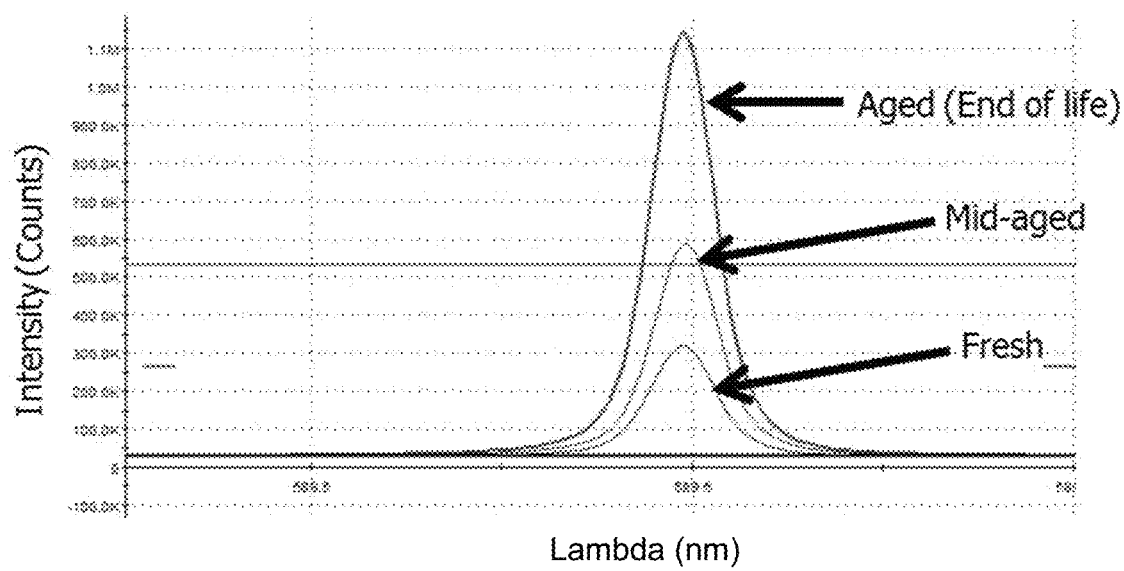
FIG. 4 provides the results of ICP-OES spectrometry measurements for sodium concentration in a fresh, mid-life and aged (end-of-life) acid copper electrodeposition solution (Solution B) of Example 2.

An acid copper electrodeposition solution (Solution B) used for advanced wafer level packaging was tested. Solution B was a solution for manufacturing of Cu interconnect in a multi-chip logic device. Sodium concentrations of Solution B were analyzed using a Spectro Blue ICP-OES spectrometer (manufactured by Spectro Analytics®). The sodium peak for Solution B was 589.59 nm, which was used for further analysis. The concentration of sodium was measured in both fresh Solution B, aged (mid-life) Solution B, and aged (end-of-life) Solution B. Fresh Solution B contained 12 mg/L of sodium. Aged (mid-life) Solution B contained 20.9 mg/L of sodium. Aged (end-of-life) Solution B contained 83 mg/L of sodium. The test results are summarized in FIG. 4. Additive turnover was calculated as follows:

Fresh Solution B sodium concentration: 12 mg/L
Aged (mid-life) Solution B sodium concentration: 20.9 mg/L
Aged (end-of-life) Solution B sodium concentration: 44.5 mg/L
Additive Turnover Aged (mid-life) Solution B: 20.9/12=1.7
Additive Turnover Aged (end-of-life) Solution B: 44.5/12=3.7

In addition to the various embodiments depicted, the disclosed subject matter is also directed to other embodiments having other combinations of the features disclosed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the disclosed subject matter and its equivalents.

What is claimed is:

1. A method for measuring additive turnover of a solution, comprising:
   providing an electrodeposition solution comprising a salt of an organic additive and a plurality of breakdown products of the salt of the organic additive, wherein the plurality of breakdown products comprise at least one inorganic component and at least one organic component;
   measuring a concentration of the at least one inorganic component; and
   determining the additive turnover of the solution based on the concentration of the at least one inorganic component in the solution.

2. The method of claim 1, wherein the organic additive comprises a brightener, an accelerator, a leveler, a suppressor, a grain refiner, a wetter, a carrier, a stress reducer, a hardener, a softener, or a combination thereof.

3. The method of claim 1, wherein the at least one inorganic component is an ion.

4. The method of claim 1, wherein the at least one inorganic component comprises a metal.

5. The method of claim 3, wherein the at least one inorganic component comprises sodium or potassium.

6. The method of claim 1, wherein the solution is an acid copper electrodeposition solution.

7. The method of claim 1, wherein the concentration of the at least one inorganic component is measured by atomic absorbance spectroscopy (AAS), microwave plasma (MP), inductively coupled plasma (ICP), ion chromatography (IC), capillary electrophoresis (CE), or ion selective electrode (ISE) potentiometry.

8. The method of claim 1, further comprising adjusting a concentration of the organic additive based on the additive turnover of the solution.

9. The method of claim 8, wherein based on the additive turnover of the solution at least a portion of the solution is removed, and at least a portion of the solution is replenished.

10. The method of claim 1, further comprising determining an end of life of the solution based on the additive turnover of the solution.

11. The method of claim 1, further comprising adjusting the concentration of the organic additive based on the additive turnover of the solution, metal turnover of the solution, and concentration of at least one organic component of the breakdown products of the organic additive.

* * * * *